United States Patent [19]

Beckhaus et al.

[11] Patent Number: 5,728,880
[45] Date of Patent: Mar. 17, 1998

[54] PROCESS FOR THE SEPARATION OF HIGH-BOILING MATERIALS FROM THE REACTION MIXTURE GENERATED DURING THE PRODUCTION OF DIAMINOTOLUENE

[75] Inventors: Heiko Beckhaus, Leverkusen; Harro Witt, Kuden; Uwe-Jens Zarnack, Brunsbüttel; Gerd Greger, Kempen, all of Germany

[73] Assignee: Bayer Aktiengesellschaft, Leverkusen, Germany

[21] Appl. No.: 806,139

[22] Filed: Feb. 25, 1997

[30] Foreign Application Priority Data

Mar. 5, 1996 [DE] Germany ............... 196 08 443.1

[51] Int. Cl.$^6$ ..................... C07C 209/84; C07C 209/86
[52] U.S. Cl. .................... 564/305; 564/420; 564/421; 564/422; 564/423; 564/424; 203/71; 203/80
[58] Field of Search .................... 564/420, 421, 564/422, 423, 424, 305

[56] References Cited

U.S. PATENT DOCUMENTS

| | | | |
|---|---|---|---|
| 3,428,531 | 2/1969 | Dietz | 564/424 X |
| 3,546,296 | 12/1970 | Gobron et al. | 260/580 |
| 3,781,373 | 12/1973 | Gorbon et al. | 260/635 C |

FOREIGN PATENT DOCUMENTS

| | | |
|---|---|---|
| 631964 | 5/1962 | Belgium . |
| 661047 | 3/1964 | Belgium . |
| 661946 | 4/1964 | Belgium . |
| 1542544 | 8/1972 | Germany . |
| 768111 | 2/1957 | United Kingdom . |

*Primary Examiner*—Richard L. Raymond
*Attorney, Agent, or Firm*—Joseph C. Gil; Lyndanne M. Whalen

[57] ABSTRACT

Amine mixtures generated during the production of diaminotoluene by hydrogenating dinitrated aromatic compounds are treated to separate high boiling materials from the desired amine products. In this process, any water of reaction and any solvent are first removed from the diaminotoluene isomer mixture (TDA mixture). The low-boiling TDA isomers are then separated using a TDA isomer distillation column. In the process of the present invention, the bottom phase remaining after the initial distillation contains a mixture of m-TDA and high-boiling materials. This bottom phase is separated and concentrated until the high-boiling material content is from approximately 25 to 60 wt. %. This concentrated bottom phase is then mixed with o-TDA in a ratio of 1:1 to 1:5 and a m-/o-TDA mixture is removed by distillation. The m-/o-TDA mixture thus recovered is then returned to the TDA isomer distillation column.

9 Claims, 2 Drawing Sheets

PROCESS FOR THE SEPARATION OF HIGH-BOILING MATERIALS FROM THE REACTION MIXTURE GENERATED DURING THE PRODUCTION OF DIAMINOTOLUENE

BACKGROUND OF THE INVENTION

This invention relates to a process for the working up of amine mixtures such as those generated during the hydrogenation of technical aromatic dinitrated compounds by distillation. During isomer separation in accordance with this process, the organic compounds boiling at a temperature higher than the boiling point of meta-toluene diamine (high-boiling materials) occur as a bottom product containing only a small proportion of meta-toluene diamine (hereinafter referred to as "m-TDA") and an elevated proportion of the highly volatile ortho-diaminotoluene (hereinafter referred to as "o-TDA").

It is known that aromatic diamines may be produced by catalytic hydrogenation of appropriate dinitrated aromatic compounds. (See, for example, DE-OS 1,542,544; BE Patents 631,964; 661,047; and 661,946; French Patent 1,359,438 and GB Patent 768,111.) Hydrogenation may be performed using solvents such as low boiling alcohols (e.g., methanol, ethanol and isopropanol) or saturated hydrocarbons (e.g., tetrahydrofuran). Hydrogenation may also be carried out without using such foreign solvents. Hydrogenation may be conducted using catalysts dispersed in the reaction mixture which are then separated by settling or filtration and are optionally returned to the process.

Until now, the hydrogenation reaction mixture (after any auxiliary solvent and water of reaction were separated) has been worked up by subjecting the mixture of aromatic diamines with any organic impurities still present to isomer separation under vacuum in a TDA distillation column. In such processes, the principal product is discharged as a bottom product. The low-boiling secondary compounds, such as ring-hydrogentated TDA and the ortho isomers of toluene diamine (TDA), are separated at the top of the column and sent for further chemical or thermal utilization.

SUMMARY OF THE INVENTION

It is an object of the present invention to provide a process for separating high-boiling secondary compounds from distillable m-TDA isomers generated during the production of diaminotoluene.

It is also an object of the present invention to provide a process for recovering m-TDA from the reaction mixture generated by hydrogenating aromatic dinitro compounds such as dinitrotoluene in which a thermally usable organic residue containing a small amount of the principal product (i.e., m-TDA) is obtained.

These and other objects which will be apparent to those skilled in the art are accomplished by distilling the reaction mixture generated by hydrogenating a dinitrated aromatic compound such as dinitrotoluene to separate the low boiling meta and ortho isomers from the high boiling materials present. The high boiling materials and some m-TDA which remain as a bottom phase after this distillation are then concentrated and subsequently mixed with o-TDA or an isomeric mixture of TDA containing o-TDA. This mixture is then distilled to remove o-TDA and m-TDA. One of the advantages of this process is that the additional energy input for the separation of high-boiling components is very low due to the use of an entraining agent, which belongs already to the process.

DETAILED DESCRIPTION OF THE PRESENT INVENTION

Figure 1:
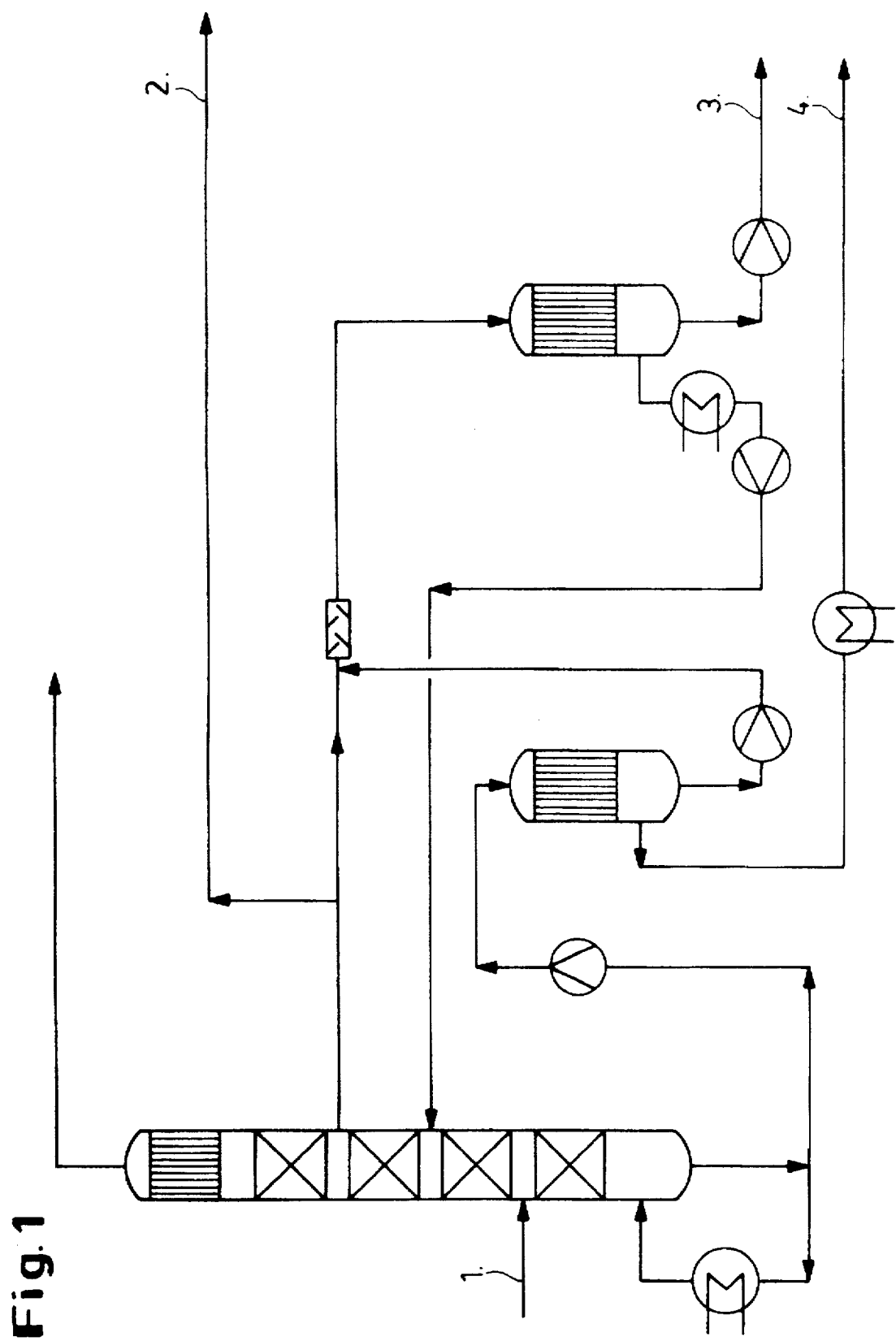
FIG. 1 is a schematic representation of the apparatus used to carry out the process of the present invention as described in Example 1.

The present invention relates to a process for working up amine mixtures generated during the production of diaminotoluene by hydrogenating dinitrated aromatic compounds. In this process, any optional solvent and water of reaction are removed from the TDA isomer mixture and then the low-boiling TDA isomers are separated as an o-TDA and m-TDA isomer fraction using a TDA isomer distillation column. The bottom phase remaining after this separation of the o-TDA and m-TDA isomer fraction is a mixture of m-TDA and high-boiling materials. This bottom phase is then concentrated to a high-boiling material content of approximately 25 to 60 wt. %. The concentrated bottom phase is then mixed in a ratio of 1:1 to 1:5 with an ortho isomer mixture and a meta-/ortho-TDA (m-/o-TDA) mixture is removed by distillation. The m-/o-TDA mixture removed by distillation is then returned to the TDA isomer distillation column.

The bottom product ultimately obtained by this process may be mixed with organic materials to be thermally utilized and, after interim storage, is thermally utilized. The bottom product ultimately obtained by the process of the present invention advantageously contains substantially less m-TDA than that obtained by other methods. In accordance with the present invention, the m-TDA content of the final bottom product is generally below 10 wt. %.

The starting materials for the process of the present invention are amine solutions such as those generated during the hydrogenation of dinitrated aromatic compounds. The amine mixtures used in the process of the present invention are preferably those generated during the hydrogenation of technical dinitrotoluenes, particularly those mixtures from which any auxiliary solvents used during the hydrogenation (e.g., simple alcohols) and any water of reaction have already been removed by distillation. These diamines include pure 2,4-diaminotoluene and the technical mixtures of toluene diamine having TDA isomer compositions of approximately 92 to 96% meta isomer, 3 to 5% ortho isomer, <1% para isomer and 0.2 to 2% high-boiling materials, in which the sum of the percentages is 100%.

The process of the present invention may be performed using a distillation column equipped with a woven packing. Such distillation column preferably has from 30 to 60, most preferably from 45 to 55 theoretical plates. The column is generally operated at a bottom temperature of from 180° to 220° C. and a pressure (at the top of the column) of from 3,000 to 120,000 Pa·s. The specific temperature and pressure used are, however, obviously dependent upon the nature of the mixtures to be worked up, the vapor to be obtained and upon the desired vapor temperature. The heat of condensation of the vapors may thus vary as a function of energy recovery by a fractionating column at the top of the column.

The crude TDA mixture from which water has been removed may be introduced into the TDA distillation column in liquid or gaseous form. In this distillation column, the low-boiling TDA isomers are separated as a pure, approximately 95 to 99 wt. % m-/o-isomer fraction. In the case of liquid feed, a column bottom product containing approximately 98% m-TDA and approximately 2% high-boiling materials remains. The column bottom product is concentrated in a downstream evaporator stage to approximately 50% high-boiling materials. The distilled m-TDA recovered during such concentration may then be Δcondensed and discharged for further use. The remaining high-boiling concentrate is mixed (e.g., by using a mixing unit) with the o-TDA removed by distillation in the distillation column in a manner such that the stripped m-/o-TDA mixture is separated in a downstream evaporator stage. These vapors, preferably after they have been condensed, may then be returned to a suitable point in the TDA isomer distillation column. The m-TDA in the bottom product containing approximately 50% high-boiling materials and 10% m-TDA is thus advantageously largely replaced by the o-TDA, which is present in an amount of approximately 40%.

If, after water has been removed, the TDA isomers are evaporated in a pre-concentration stage to an extent that the discharged product contains approximately 50% high-boiling materials, the TDA isomer vapors are introduced into the distillation column and accordingly separated into the ortho- and meta-TDA isomers. The column bottom product then contains the m-TDA from which the high-boiling materials have been removed. The m-TDA may then be further processed. The high-boiling concentrate obtained in the pre-concentration stage is, as described above, mixed with distilled o-TDA using a mixing unit in a manner such that the m-/o-TDA mixture is separated in a downstream evaporator stage and these vapors (preferably condensed) are returned to a suitable point in the distillation column.

The following examples illustrate the process of the present invention in greater detail.

EXAMPLES

Example 1

2.3 kg/h of a reaction mixture from the hydrogenation of dinitrotoluene from which water and solvent had been removed were introduced at the 8th plate into a DN 50 packed column having 50 theoretical distillation stages. The mixture had a composition of 76.5 wt. % 2,4-diaminotoluene, 18.5 wt. % 2,6-diaminotoluene, 4 wt. % ring-hydrogenated TDA and 0.9 wt. % high-boiling materials (stream 1 in FIG. 1 ). The column was operated at an overhead pressure of 8,000 Pa·s and a bottom temperature of 203° C. The o-TDA was completely condensed at an overhead temperature of 160° C. and 0.3 kg/h of 99 wt. % product were drawn off as a liquid at the 45th plate at a controlled temperature. The 20 g/h of vapors passing through the dephlegmator contained approximately 30 wt. % ring-hydrogenated TDA in o-TDA. These vapors were condensed and discharged at approximately 100° C. into the thermal utilization receiver.

In a downstream falling-film evaporator, the m-TDA was removed from the bottom product made up of 99 wt. % of 2,4-/2,6-diaminotoluene mixture and 1 wt. % of high-boiling materials, under a constant vacuum to such an extent that the high-boiling components were concentrated to up to approximately 50 wt. %. The vapors, 2.15 kg/h of m-TDA, were condensed and discharged for further processing or sale (stream 4 in FIG. 1). The concentrate (70 g/h) was mixed with the 250 g/h of o-TDA discharged as a liquid at a ratio of 1:3.5 and the TDA isomers were vaporized together at a pressure of 8,000 Pa·s. The vapors (250 g/h) were condensed and returned as a liquid to the 25th plate of the isomer column. 70 g/h of the bottom product which was made up of 50 wt. % high-boiling materials, 40 wt. % o-TDA and 10 wt. % m-TDA (stream 3 in FIG. 1 ) were introduced into the thermal utilization receiver in which an organic mixture principally composed of o-TDA (stream 2 in FIG. 1) was present to obtain a mixture useful for combustion having a caloric value of approximately 33,000 kcal/kg.

Example 2

Figure 2:
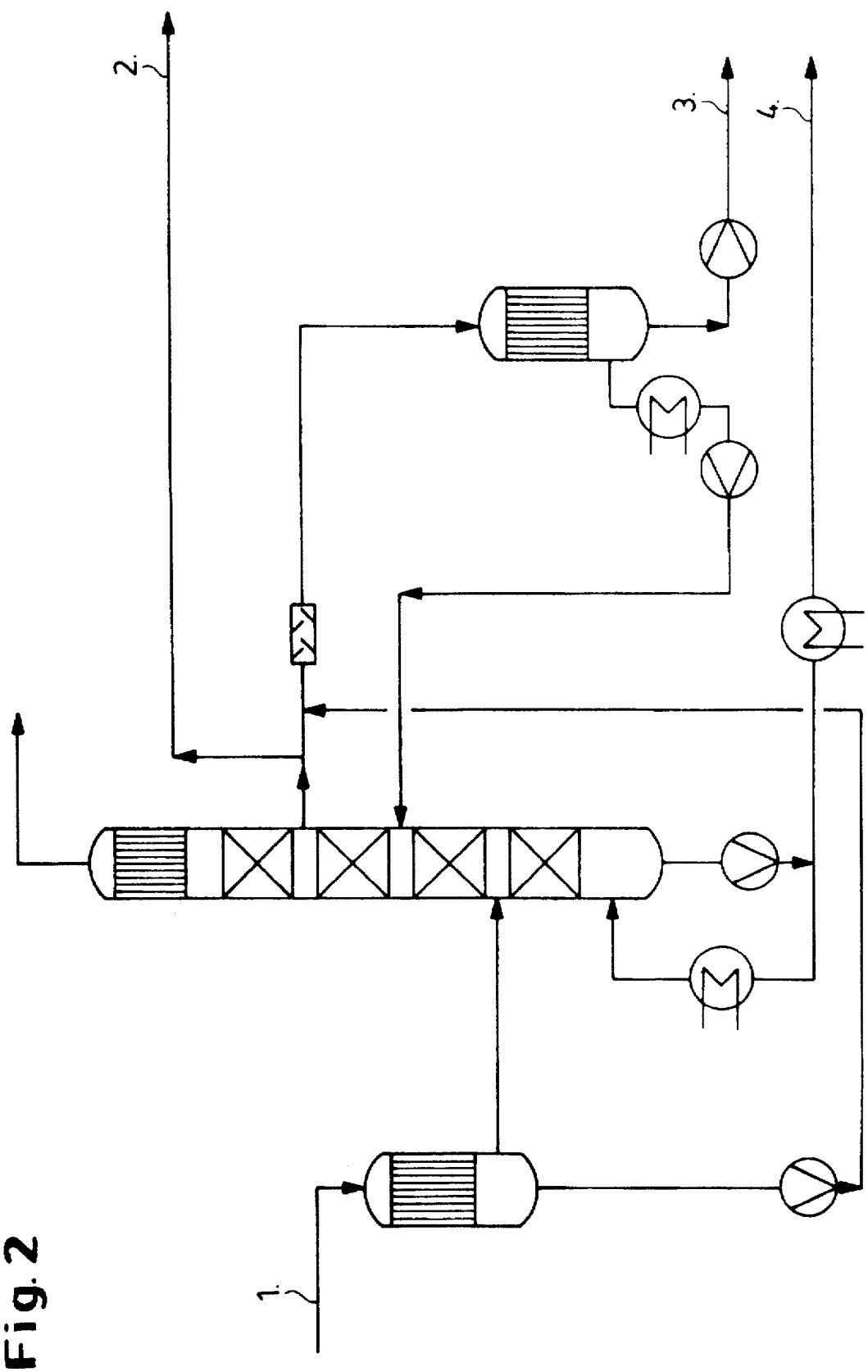
FIG. 2 is a schematic representation of apparatus used to carry out the process of the present invention as described in Example 2.

2.2 kg/h of a stream of vapor from a falling-film evaporator upstream from the isomer column and which was composed of 77.9 wt. % 2,4-diaminotoluene, 17.6 wt. % 2,6-diaminotoluene, 4.2 wt. % remaining diaminotoluenes and 0.1 wt. % ring-hydrogenated TDA (stream 1 in FIG. 2) were introduced into a DN 50 packed column with 50 theoretical distillation stages. The TDA isomers were separated as in Example 1 by distillation at a column overhead pressure of 4,000 Pa·s and a bottom temperature of 192° C. The high-boiling materials were directly removed from the bottom product and the bottom product was cooled to approximately 120° C. for further processing or stored for sale (stream 4 in FIG. 2).

The high-boiling component concentrate (70 g/h) discharged from the upstream falling-film evaporator was mixed with ortho-TDA drawn off as a liquid (250 g/h) in a ratio of 1:3.5 and the TDA isomers were vaporized together at a pressure of 4,000 Pa·s. The vapors (250 g/h) were condensed and returned as a liquid to the 25th plate of the isomer column. 70 g/h of the bottom product which was composed of 50 wt. % high-boiling materials, 40 wt. % o-TDA and 10 wt. % m-TDA (stream 3 in FIG. 2) was introduced into the thermal utilization receiver. In the thermal utilization receiver, an organic mixture principally composed of o-TDA (stream 2 in FIG. 2) having a caloric value of approximately 33,000 kcal/kg was obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for separating low-boiling isomers of toluene diamine from an amine mixture produced by hydrogenating dinitrated aromatic compounds comprising:

a) removing any water of reaction and any solvent present in the amine mixture, b) introducing the mixture treated in accordance with a) into a distillation column, c) separating pure, low-boiling meta and ortho isomers of toluene diamine from a bottom phase containing meta-toluene diamine and high-boiling materials, d) concentrating the bottom phase from c) until the high boiling materials are present in an amount of from about 25 to about 60% by weight, e) mixing the concentrated bottom phase from d) with ortho-toluene diamine in an amount such that the ratio of concentrated bottom phase to ortho-toluene diamine is from about 1:1 to about 1:5, f) distilling the mixture from e) to remove a mixture of meta- and ortho-toluene diamine, and g) introducing the meta- and ortho-toluene diamine mixture removed in f) to the distillation column used in b).

2. The process of claim 1 in which step d) is carried out in an evaporator and/or stripping column having from 2 to 10 theoretical plates.

3. The process of claim 2 in which step f) is carried out in a distillation column having from 2 to 30 theoretical plates.

4. The process of claim 2 in which step f) is carried out in a distillation column having from 2 to 10 theoretical plates.

5. The process of claim 1 in which step f) is carried out in a distillation column having from 2 to 30 theoretical plates.

6. The process of claim 1 in which step f) is carried out in a distillation column having from 2 to 10 theoretical plates.

7. The process of claim 1 in which step d) is carried out in a manner such that the ratio of high boiling materials to meta-toluene diamine is from 1:1 to 1:10.

8. The process of claim 1 in which after the distillation of step f), a residue in which the ratio of high-boiling material to ortho-toluene diamine is from 5:1 to 1:10 remains.

9. The process of claim 1 in which each of the distillation steps is carried out at a column overhead pressure of from 3,000 to 120,000 Pa·s.

* * * * *